(12) United States Patent
Kuramochi

(10) Patent No.: US 10,772,771 B2
(45) Date of Patent: Sep. 15, 2020

(54) ABSORBENT ARTICLE

(71) Applicant: DAIO PAPER CORPORATION, Ehime (JP)

(72) Inventor: Mihoko Kuramochi, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 324 days.

(21) Appl. No.: 15/743,040

(22) PCT Filed: Aug. 17, 2016

(86) PCT No.: PCT/JP2016/073964
§ 371 (c)(1),
(2) Date: Jan. 9, 2018

(87) PCT Pub. No.: WO2017/030136
PCT Pub. Date: Feb. 23, 2017

(65) Prior Publication Data
US 2018/0221220 A1 Aug. 9, 2018

(30) Foreign Application Priority Data

Aug. 17, 2015 (JP) ................................. 2015-160366
Aug. 8, 2016 (JP) ................................. 2016-155238

(51) Int. Cl.
*A61F 13/512* (2006.01)
*B32B 3/30* (2006.01)
(Continued)

(52) U.S. Cl.
CPC ...... *A61F 13/512* (2013.01); *A61F 13/15203* (2013.01); *A61F 13/5116* (2013.01);
(Continued)

(58) Field of Classification Search
CPC ............ A61F 13/51104; A61F 13/5123; A61F 13/5126; A61F 13/5116; B32B 3/30
See application file for complete search history.

(56) References Cited

U.S. PATENT DOCUMENTS 4,741,941 A * 5/1988 Englebert ............... A47L 13/16
15/209.1
5,705,249 A * 1/1998 Takai ....................... B32B 3/30
428/94

(Continued)

FOREIGN PATENT DOCUMENTS

| JP | H4-89054 | 3/1992 |
| JP | 2002-173863 | 6/2002 |

(Continued)

OTHER PUBLICATIONS

International Search Report for PCT/JP2016/073964 dated Oct. 18, 2016.

*Primary Examiner* — Susan S Su
(74) *Attorney, Agent, or Firm* — IPUSA, PLLC

(57) ABSTRACT

A sanitary napkin (1) includes an absorbent (4) interposed between a liquid permeable top sheet (3) and a back sheet (2), wherein the liquid permeable top sheet (3) has multiple protruding parts (10) that protrude towards a skin side and that are formed at intervals, embossed parts (11) compressed from the skin side, and opening parts (12) that penetrate the liquid permeable top sheet (3), the embossed parts (11) and opening parts (12) being formed, around the protruding parts (10), to be separate from each other. Skin side extending parts (13) are provided at peripheries of the opening parts (12) such that the skin side extending parts (13) protrude towards the skin side at heights lower than heights of the protruding parts (10). In a plan view of the liquid permeable top sheet (3), the protruding parts (10) are arranged in a zigzag pattern, the opening parts (12) are arranged at areas (Continued)

four sides of which are surrounded by the protruding parts (10), and the embossed parts (11) are continuously or non-continuously arranged, between the adjacent opening parts (12), along directions that connect the adjacent opening parts (12).

9 Claims, 9 Drawing Sheets

(51) Int. Cl.
*B32B 5/26* (2006.01)
*A61F 13/511* (2006.01)
*A61F 13/15* (2006.01)
*A61F 13/472* (2006.01)

(52) U.S. Cl.
CPC ....... *A61F 13/51104* (2013.01); *A61F 13/472* (2013.01); *A61F 2013/51178* (2013.01); *B32B 3/30* (2013.01); *B32B 5/26* (2013.01); *B32B 2307/726* (2013.01); *B32B 2555/02* (2013.01)

(56) References Cited

U.S. PATENT DOCUMENTS

| | | | |
|---|---|---|---|
| 6,719,742 B1* | 4/2004 | McCormack | A61F 13/51462 |
| | | | 604/385.01 |
| 7,518,032 B2* | 4/2009 | Seyler | A61F 13/53713 |
| | | | 604/383 |
| 7,569,264 B2* | 8/2009 | Toyoshima | A61F 13/5116 |
| | | | 428/156 |
| 9,849,602 B2* | 12/2017 | Cree | A61F 13/5121 |
| 10,092,461 B2* | 10/2018 | Seyler | A61F 13/53713 |
| 10,376,429 B2* | 8/2019 | Hao | A61F 13/45 |
| 2001/0014796 A1* | 8/2001 | Mizutani | A61F 13/512 |
| | | | 604/367 |
| 2002/0029025 A1* | 3/2002 | Furuya | A61F 13/51121 |
| | | | 604/378 |
| 2003/0114818 A1* | 6/2003 | Benecke | A61F 13/505 |
| | | | 604/378 |
| 2003/0124311 A1* | 7/2003 | Cree | B26F 1/24 |
| | | | 428/138 |
| 2003/0143376 A1* | 7/2003 | Toyoshima | A61F 13/51104 |
| | | | 428/156 |
| 2003/0181882 A1* | 9/2003 | Toyoshima | A61F 13/51104 |
| | | | 604/367 |
| 2004/0127875 A1* | 7/2004 | Hammons | A61F 13/51104 |
| | | | 604/385.01 |
| 2005/0003152 A1* | 1/2005 | Thomas | A61F 13/4902 |
| | | | 428/131 |
| 2005/0256475 A1* | 11/2005 | Komatsu | A61F 13/512 |
| | | | 604/378 |
| 2008/0114317 A1* | 5/2008 | Seyler | A61F 13/53713 |
| | | | 604/369 |
| 2010/0249740 A1 | 9/2010 | Miyamoto et al. | |
| 2012/0064280 A1* | 3/2012 | Hammons | A61F 13/15707 |
| | | | 428/85 |
| 2013/0158497 A1* | 6/2013 | Yamaguchi | A61F 13/51104 |
| | | | 604/378 |
| 2014/0336608 A1* | 11/2014 | Hao | B32B 3/30 |
| | | | 604/385.01 |
| 2014/0358101 A1* | 12/2014 | Kanya | D04H 1/4291 |
| | | | 604/366 |
| 2016/0038351 A1* | 2/2016 | Cecchetto | B29C 51/20 |
| | | | 428/134 |
| 2016/0257091 A1* | 9/2016 | Fornoni | B32B 37/14 |
| 2017/0297292 A1* | 10/2017 | Maschino | B32B 5/022 |
| 2018/0140479 A1* | 5/2018 | Uda | A61F 13/15 |
| 2018/0193208 A1* | 7/2018 | Hashimoto | A61F 13/51 |
| 2018/0200123 A1* | 7/2018 | Xie | B32B 5/022 |
| 2018/0369028 A1* | 12/2018 | Cecchetto | A61F 13/5116 |
| 2019/0117473 A1* | 4/2019 | Rosati | A61F 13/496 |
| 2019/0142654 A1* | 5/2019 | Uda | A61F 13/15203 |
| | | | 604/383 |
| 2019/0240085 A1* | 8/2019 | Miyama | A61F 13/512 |

FOREIGN PATENT DOCUMENTS

| | | |
|---|---|---|
| JP | 2005-334374 | 12/2005 |
| JP | 2008-73396 | 4/2008 |
| JP | 2009-172354 | 8/2009 |
| JP | 2013-129937 | 7/2013 |
| WO | 2015/098373 | 7/2015 |

\* cited by examiner (SKIN SIDE)

(NON-SKIN SIDE)

(SKIN SIDE)

(NON-SKIN SIDE)

ABSORBENT ARTICLE

TECHNICAL FIELD

The present invention relates to an absorbent article such as a sanitary napkin, a panty liner, an incontinence pad, and a disposable diaper for absorbing body fluids such as menstrual blood, vaginal discharge, and urine and specifically, relates to an absorbent article on a surface of which protrusions and recesses are provided.

BACKGROUND ART

Conventionally, surface materials of absorbent articles, to which appropriate embossment patterns are given in accordance with various objects such as an object to reduce a contact area with a skin to reduce a wet feeling or an object to express a texture to enhance feeling characteristics, are provided, to the market. Further, as such a surface material, a material is developed on which appropriate openings are formed in accordance with various objectives such as enhancing the absorption speed of a body fluid or removing a liquid residue on the surface to resolve a sticky feeling. For example, the following Patent Documents 1 and 2 are described.

The following Patent Document 1 describes an article where liquid guiding pipes having upper surface and lower surface openings are arrayed to extend below and skin contact areas connected to peripheries of the upper surface openings of the liquid guiding pipes. Further, the following Patent Document 2 describes a non-woven fabric, in which an upper layer located at a front surface side and a lower layer located adjacent to the upper layer and located at a back surface side are formed together, and having multiple openings. The average fiber diameter of fibers constituting the upper layer is less than an average fiber diameter of the fibers constituting the lower layer. The lower layer includes fibers having a fiber diameter in a range of from 5 μm to 20 μm by 70% to 30% by weight and includes fibers having a fiber diameter in a range of from 20 μm to 40 μm by 30% to 70% by weight such that these fibers have different fiber diameters, and the upper layer reaches the back surface of a front surface sheet at the peripheries of the openings.

RELATED-ART DOCUMENTS

Patent Document

Patent Document 1: Japanese Examined Patent Publication No. 2849179
Patent Document 2: Japanese Examined Patent Publication No. 4023996

SUMMARY OF THE INVENTION

Problem to be Solved by the Invention

However, in the article described in the above described Patent Document 1, the skin contact areas are formed to be flat. Therefore, the peripheries of the openings directly contact a skin and a texture feeling is not good. In particular, in a case where an opening process is applied by heat or ultrasound, the peripheries of openings are hardened, and therefore the texture feeling is worsened. Further, when body fluids are absorbed, the body fluids are likely to remain at the flat skin contact areas and the liquid may remain on the surface.

Further, in the article described in the above described Patent Document 2, in a case where a highly viscous body fluid such as viscous menstrual blood is absorbed, the highly viscous body fluid is likely to remain at a curved rib part having a protruding shape or at a groove around an opening, and the liquid may remain on the surface.

Hence, a main object of the present invention is to provide an absorbent article such that a texture feeling is favorable and a liquid residue on a surface is reduced.

Means to Solve the Problem

In order to solve the above described problem, as the present invention according to claim 1, a provided absorbent article includes an absorbent interposed between a liquid permeable top sheet and a back sheet. The absorbent article is characterized in that the liquid permeable top sheet has multiple protruding parts that protrude towards a skin side and that are formed at intervals, embossed parts compressed from the skin side, and opening parts that penetrate the liquid permeable top sheet, the embossed parts and the opening parts being formed, around the protruding parts, to be separate from each other.

According to the invention recited in the above described claim 1, the liquid permeable top sheet has the multiple protruding parts that protrude towards the skin side and are formed at the intervals. Therefore, a contact area between the liquid permeable top sheet and a skin surface is reduced and cushioning characteristics are enhanced. Thereby, a texture becomes favorable.

Further, the embossed parts and the opening parts are formed, around the protruding parts, to be separate from each other. Therefore, through capillary action due to a density gradient of fibers, body fluids absorbed by the protruding parts can be promptly diffused towards the embossed parts, the body fluids can be easily transferred towards the absorbent through the embossed parts and the opening parts, and a liquid residue on the surface can be reduced.

As the present invention according to claim 2, the absorbent article recited in claim 1 is provided wherein skin side extending parts are provided at peripheries of the opening parts such that the liquid permeable top sheet protrudes towards the skin side at heights lower than heights of the protruding parts.

According to the invention recited in the above described claim 2, the skin side extending parts, which protrude towards the skin side, are provided at the peripheries of the opening parts. Therefore, body fluids diffused towards the embossed parts contacts the skin side extending parts, are taken into the opening parts by capillary action, and are transferred towards the absorbent. Further, heights of the skin side extending parts, which protrude at the peripheries of the opening parts towards the skin side, are formed to be lower than heights of the protruding parts. Therefore, tips of the skin side extending parts are not in contact with a skin and a favorable texture feeling can be maintained.

As the present invention according to claim 3, the absorbent article recited in claim 1 or 2 is provided wherein in a plan view of the liquid permeable top sheet, the protruding parts are arranged in a zigzag pattern, the opening parts are arranged at areas four sides of which are surrounded by the protruding parts, and the embossed parts are continuously or non-continuously arranged, between the adjacent opening parts, along directions that connect the adjacent opening parts.

The invention recited in the above described claim 3 specifically represents a planar arrangement pattern of the protruding parts, the opening parts, and the embossed parts with respect to the liquid permeable top sheet. In the pattern, in addition to arranging the protruding parts in a zigzag pattern, by forming the opening parts at areas four sides of which are surrounded by the protruding parts, the opening parts are arranged in a zigzag pattern as a whole, and the embossed parts are non-continuously or continuously arranged, between the adjacent opening parts, along the directions that connect the adjacent opening parts. Thereby, body fluids, diffused from the protruding parts to the embossed parts due to a density gradient of fibers, easily transfer towards a lower layer through the embossed parts, diffuse along the embossed parts provided continuously or non-continuously along directions that connect the adjacent opening parts, and easily transfer towards the lower layer through the opening parts provided at their both end parts.

As the present invention according to claim 4, the absorbent article recited in any one of claims 1 to 3 is provided wherein the liquid permeable top sheet has a layered structure including a skin side layer located at the skin side and a non-skin side layer located at a non-skin side, a fineness of a fiber constituting the non-skin side layer is less than 2.0 dtex.

According to the invention recited in the above described claim 4, the fineness of the fiber constituting the skin side layer of the liquid permeable sheet is a fine fiber of less than 2.0 dtex. Therefore, friction with a skin can be reduced and a texture feeling can be further favorable.

As the present invention according to claim 5, the absorbent article recited in any one of claims 1 to 4 is provided wherein a second sheet is disposed adjacent to a non-skin side of the liquid permeable top sheet, and the embossed parts are formed by compressing the liquid permeable top sheet and the second sheet together, and the opening parts are formed by penetrating the liquid permeable top sheet and the second sheet together.

According to the invention recited in the above described claim 5, the second sheet is disposed adjacent to the non-skin side of the liquid permeable top sheet. In this case, with respect to the liquid permeable top sheet and the second sheet as an integral sheet, the embossed parts and the opening parts are formed such that body fluids absorbed by the liquid permeable top sheet and the second sheet are easily transferred towards the absorbent.

As the present invention according to claim 6, the absorbent article recited in claim 5 is provided wherein skin side extending parts that protrude towards the skin side are provided at peripheries of the opening parts, heights of the skin side extending parts being lower than heights of the protruding parts, the skin side extending parts being formed such that the liquid permeable top sheet and the second sheet protrude towards the skin side from the peripheries of the opening parts.

According to the invention recited in the above described claim 6, in a case where the second sheet is disposed adjacent to the non-skin side of the liquid permeable top sheet, the skin side extending parts are formed by causing the liquid permeable top sheet and the second sheet to protrude together from the peripheries of the opening parts towards the skin side. Hence, body fluids diffused along the embossed parts are taken into the opening parts by capillary action of the liquid permeable top sheet and the second sheet, and are absorbed by the absorbent.

As the present invention according to claim 7, the absorbent article recited in any one of claims 1 to 6 is provided wherein the liquid permeable top sheet has a layered structure including a skin side layer located at the skin side and a non-skin side layer located at anon-skin side, and a second sheet is disposed adjacent to a non-skin side of the non-skin side layer, and a fineness of a fiber constituting the non-skin side layer is set to be greater than a fineness of a fiber constituting the second sheet.

According to the invention recited in the above described claim 7, the liquid permeable top sheet has the layered structure including the skin side layer and the non-skin side layer, and in a case where the second sheet is disposed adjacent to the non-skin side of the non-skin side layer, the fineness of the fiber constituting the non-skin side layer is set to be greater than the fineness of the fiber constituting the second sheet. Therefore, through capillary action due to a density gradient of the fibers from the non-skin side layer of the top sheet to the second sheet, body fluid are easily transferred to from the top sheet to the second sheet.

As the invention according to claim 8, the absorbent article recited in any one of claims 1 to 7 is provided wherein the liquid permeable top sheet has a layered structure including a skin side layer located at the skin side and a non-skin side layer located at a non-skin side, and a second sheet is disposed adjacent to a non-skin side of the non-skin side layer, and strength of durability of hydrophilic oil of the skin side layer of the liquid permeable top sheet, the non-skin side layer of the liquid permeable top sheet, and the second sheet is in a relationship of the skin side layer ≤ the non-skin side layer ≤ the second sheet.

According to the invention recited in the above described claim 8, because strength of durability of hydrophilic oil of each sheet is set to have a gradient in a relationship of the skin side layer of the front sheet ≤ the non-skin side layer of the front sheet ≤ the second sheet, body fluids are favorably taken into a lower layer and a liquid residue on the surface can be reduced.

Advantage of the Invention

According to the present invention described above in details, it becomes possible to obtain a favorable texture feeling and to reduce a liquid residue on a surface.

MODE FOR CARRYING OUT THE INVENTION

In the following, embodiments of the present invention are described with reference to the accompanying drawings.

Basic Structure of Sanitary Napkin 1

Figure 1:
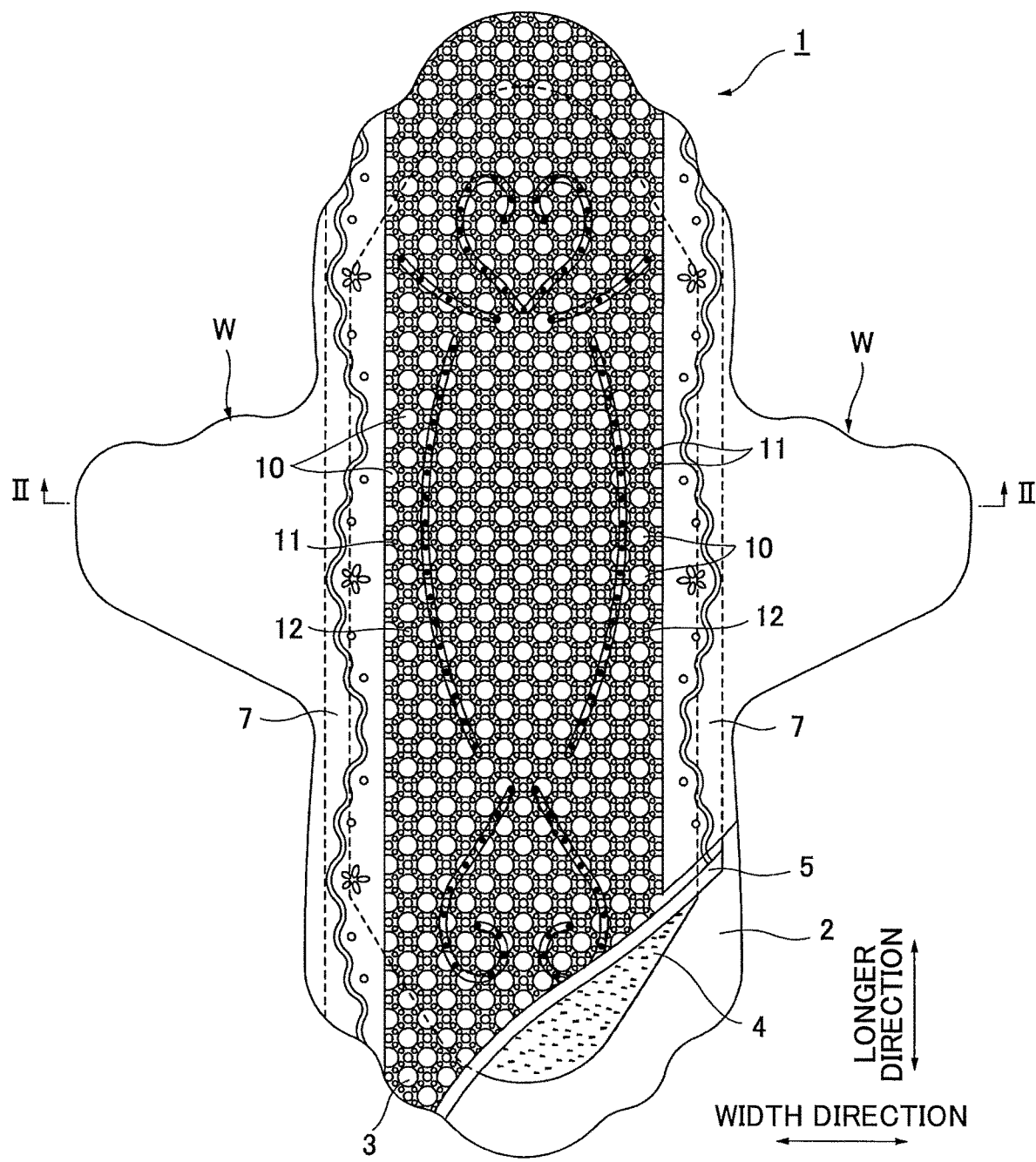
FIG. 1 is a partially broken development view of a sanitary napkin 1 according to a first embodiment.
Figure 2:
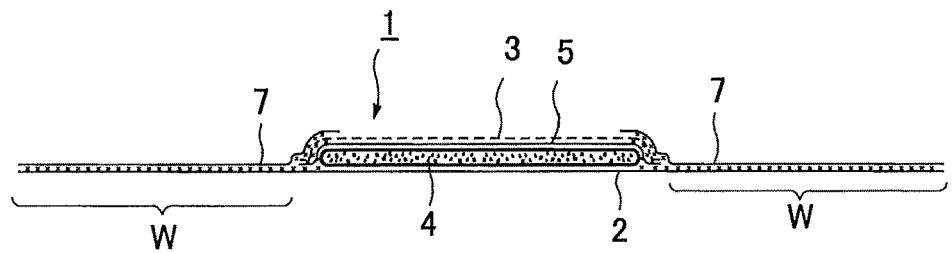
FIG. 2 is a cross-sectional view taken along a line II-II of FIG. 1.

As illustrated in FIG. 1 and FIG. 2, a sanitary napkin 1 according to the present invention includes a liquid impermeable back sheet 2 formed of a sheet such as a polyethylene sheet or a polypropylene sheet; a liquid permeable top sheet 3 that allows menstrual blood, vaginal discharge, and the like to quickly pass through; and an absorbent 4 interposed between these sheets 2 and 3 and made of pulp, such as cotton-like pulp or synthetic pulp, and includes, as needed, a hydrophilic second sheet 5 disposed adjacent to the non-skin side of the liquid permeable top sheet 3.

The structure of the sanitary napkin 1 will be described in more detail below. As the liquid impermeable back sheet 2, a sheet material having at least a waterproof property such as an olefin-based sheet such as polyethylene or polypropylene may be used. In addition, a laminate nonwoven fabric, in which a nonwoven fabric is stacked in layers on a polyethylene sheet or the like, a nonwoven fabric sheet in which a waterproof film is interposed to practically acquire liquid-impermeability (in this case, the waterproof film and the nonwoven fabric constitute the liquid impermeable back sheet), and the like can be used. In recent years, in terms of reducing dampness, a moisture permeable sheet material tends to be used. Such a water shielding and moisture permeable sheet material is a microporous sheet that is obtained by melting and kneading an inorganic filler in an olefin-based resin such as polyethylene or polypropylene to mold a sheet and stretching it uniaxially or biaxially.

As the liquid permeable top sheet 3, a nonwoven fabric may be preferably used. For example, as a material fiber constituting the nonwoven fabric, a synthetic fiber such as an olefin fiber of polyethylene, polypropylene, or the like, a polyester fiber, a polyamide fiber and the like; a regenerated fiber such as rayon or cupra; or a natural fiber such as cotton may be used, and a nonwoven fabric obtained by appropriate processing methods such as a spun lace method, a spun bond method, a thermal bond method, a melt-blown method or a needle punch method can be used. Among these processing methods, the spun lace method has an advantage in terms of flexibility, the spun bond method has an advantage in terms of a doping property, and the thermal bond method an air through method has an advantage in terms of, bulkiness and compression restorability. Further, a composite fiber may be used such as a core-in-sheath fiber including a high-melting-point fiber as a core and low-melting-point fiber as a sheath, a side-by-side fiber, or a split fiber. As described later below in details, an embossing process and an opening process are applied to the liquid permeable top sheet 3. Further, the liquid permeable top sheet 3 may have a single layer structure of one layer or a layered structure of two or more layers as described later below.

The absorbent 4 interposed between the liquid impermeable back sheet 2 and the liquid permeable top sheet 3 is formed with, for example, cotton-like pulp and a highly water absorptive polymer. As the highly water absorptive polymer, a superabsorbent polymer granular powder (SAP) or a superabsorbent polymer fiber (SAF) may be used. Examples of the pulp described above include cellulose fibers such as dissolving pulp and chemical pulp made from wood and synthetic cellulose fibers such as rayon and acetate. In terms of the function and the price, softwood pulp with a long fiber length is more preferably used than hardwood pulp. For a method of producing the absorbent 4, although fiber stacking pulp is preferably used for obtaining the desired flexibility, an air laid absorbent may be used to reduce bulk. The absorbent 4 may be surrounded by an encapsulating sheet (not illustrated) made of crepe paper sheet or a nonwoven fabric in order to retain a shape and to improve diffusivity thereof.

Further, a synthetic fiber may also be mixed in the absorbent 4. For the above described synthetic fiber, for example, a polyolefin fiber such as polyethylene or polypropylene; a polyester fiber such as polyethylene terephthalate or polybutylene terephthalate; a polyamide fiber such as nylon; and a copolymer of these polymers may be used. Also, a mixture of two types of these may be used. Further, a composite fiber may be used such as a core-in-sheath fiber including a high-melting-point fiber as a core and a low-melting-point fiber as a sheath, a side-by-side fiber, or a split fiber.

The hydrophilic second sheet 5, disposed as needed adjacent to the non-skin side of the liquid permeable top sheet 3, may be a sheet having a hydrophilic property with respect to a body fluid. Specifically, a sheet having a hydrophilic material using a regenerated fiber such as rayon or cupra or a natural fiber such as cotton can be used, or a fiber to which a hydrophilic property is added by applying, by use of a hydrophilizing agent, a surface treatment to a synthetic fiber such as an olefin fiber of polyethylene, polypropylene, or the like, a polyester fiber, or a polyamide fiber. Further, a composite fiber may be used such as a core-in-sheath fiber including a high-melting-point fiber as a core and a low-melting-point fiber as a sheath, a side-by-side fiber, or a split fiber. As described later below, the second sheet 5 is joined to the non-skin side of the liquid permeable top sheet 3 through thermal fusion bonding (embossed parts 11), and an opening process of the opening parts 12 is applied to the second sheet 5 together with the liquid permeable top sheet 3 while stacking both sheets.

It is preferable to join the second sheet 5 and the absorbent 4 together through a hot melt adhesive agent or the like. By joining the second sheet 5 and the absorbent 4, body fluids such as menstrual blood can be rapidly transferred from the second sheet 5 to the absorbent 4.

Liquid Permeable Top Sheet 3

First Embodiment

Figure 3:
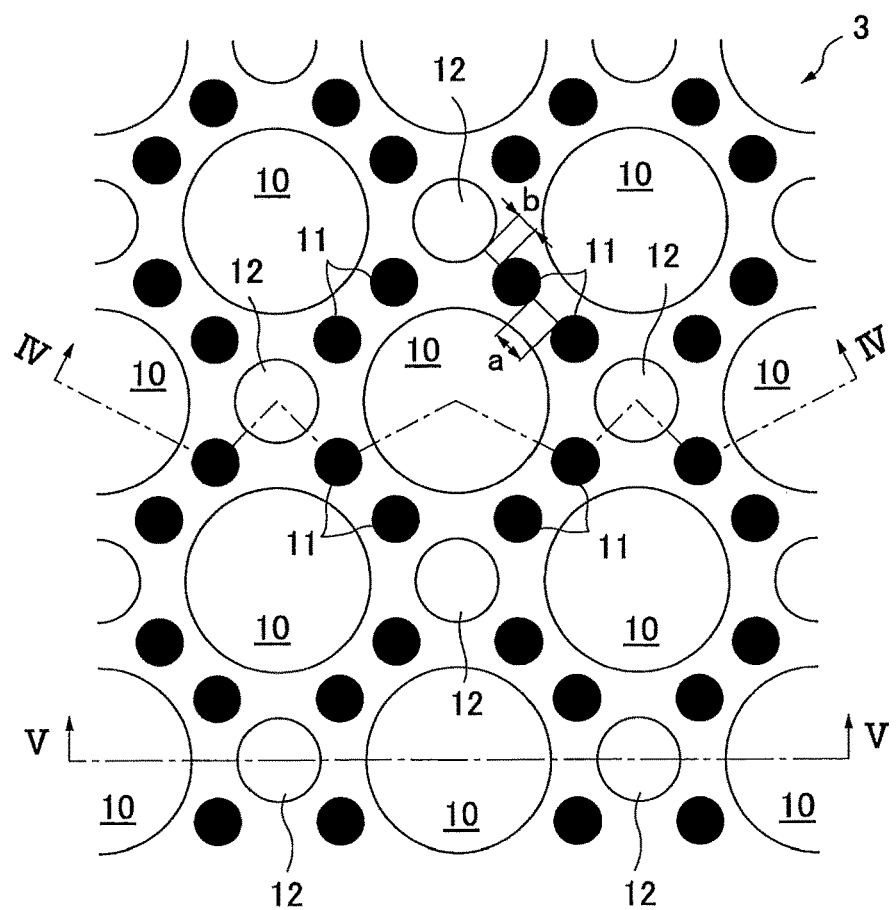
FIG. 3 is an enlarged plan view of a liquid permeable top sheet 3 according to the first embodiment.
Figure 4:
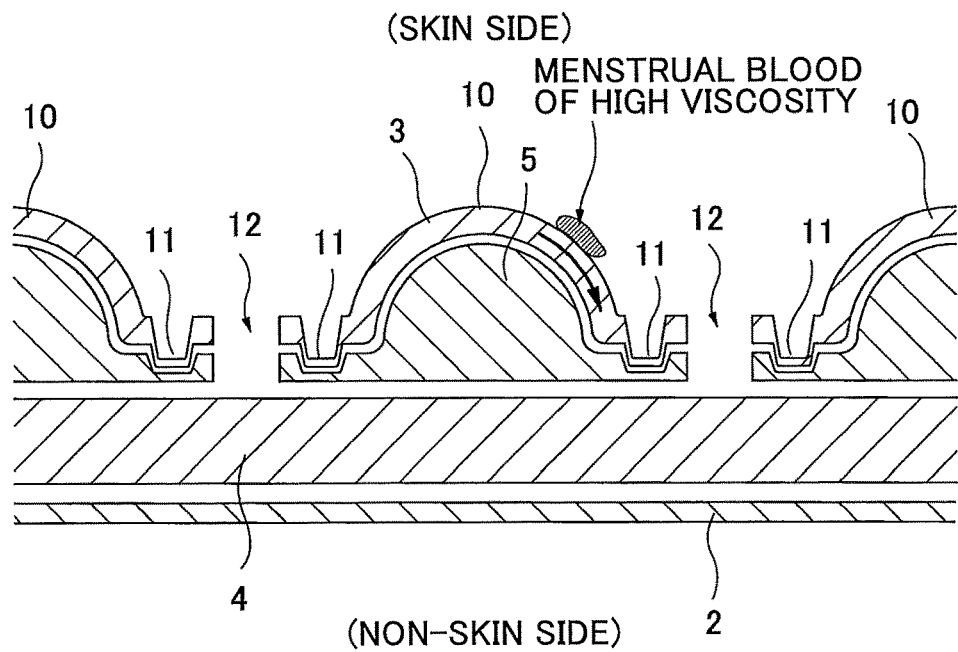
FIG. 4 is a cross-sectional view taken along a line IV-IV of FIG. 3.
Figure 5:
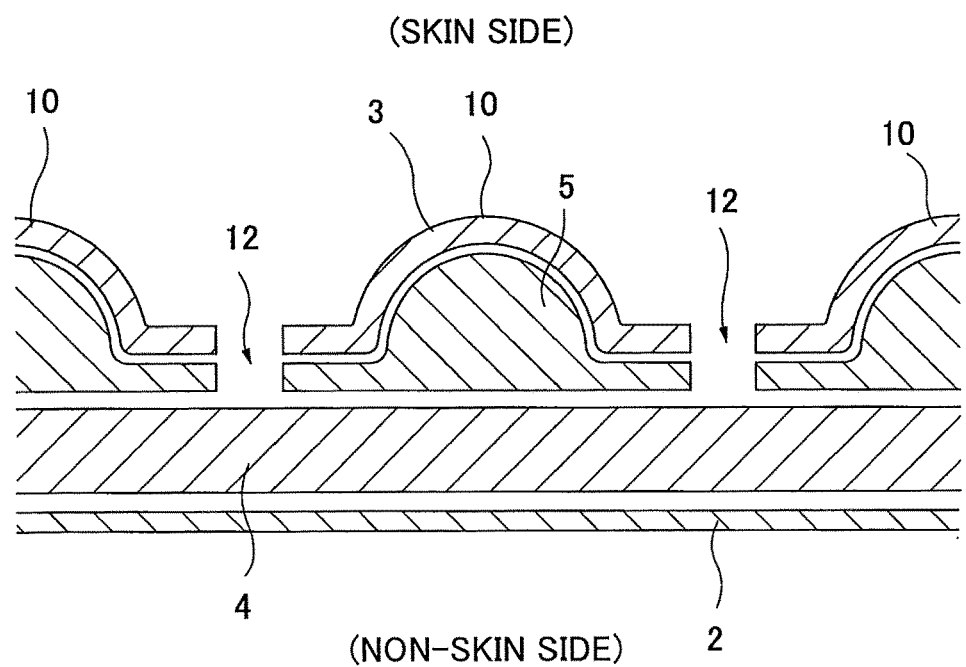
FIG. 5 is a cross-sectional view taken along a line V-V of FIG. 3.

As illustrated in FIG. 3 to FIG. 5, a liquid permeable top sheet 3 according to the first embodiment has multiple protruding parts 10 that protrude towards the skin side and that are formed at intervals, the embossed parts 11 compressed from the skin side, and opening parts 12 that penetrate the liquid permeable top sheet 3, the embossed parts 11 and the opening parts 12 being formed, around the protruding parts 10, to be separate from each other. The embossed parts 11 and the opening parts 12 being separate from each other means the embossed parts 11 and the opening parts 12 being formed at respective different areas without overlapping with each other.

In a plan view illustrated in FIG. 3, the protruding parts 10, the opening parts 12, the embossed parts 11, and the opening parts 12 are arranged with respect to the liquid permeable top sheet 3 such that, the protruding parts 10 are arranged in a zigzag pattern, one of the opening parts 12 is arranged at the central part of an area four sides, left, right, top and bottom, of which are surrounded by the protruding parts 10. Thereby, a pattern is formed in which the opening parts 12 are arranged in a zigzag pattern as a whole and, the plurality of embossed parts 11 are non-continuously arranged, between the adjacent opening parts 12, along directions that connect the adjacent opening parts 12.

Further, as illustrated in FIG. 4, in a case where the second sheet 5 is disposed adjacent to the non-skin side of the liquid permeable top sheet 3, it is preferable that, in addition to the second sheet 5 being arranged such that the skin side surface of the second sheet 5 protrudes towards the skin side along the internal surface (the non-skin side surface) of the liquid permeable top sheet 3 at the protruding parts 10, the embossed parts 11 are formed by compressing the liquid permeable top sheet 3 and the second sheet 5 together, and the opening parts 12 are formed by penetrating the liquid permeable top sheet 3 and the second sheet 5 together.

Figure 6:
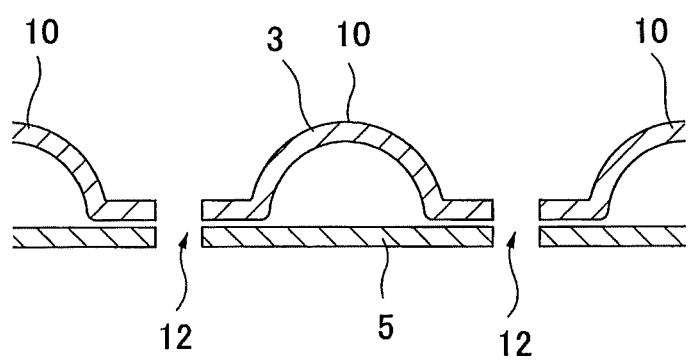
FIG. 6 is a cross-sectional view of protruding parts 10 according to a variation example.
Figure 7:
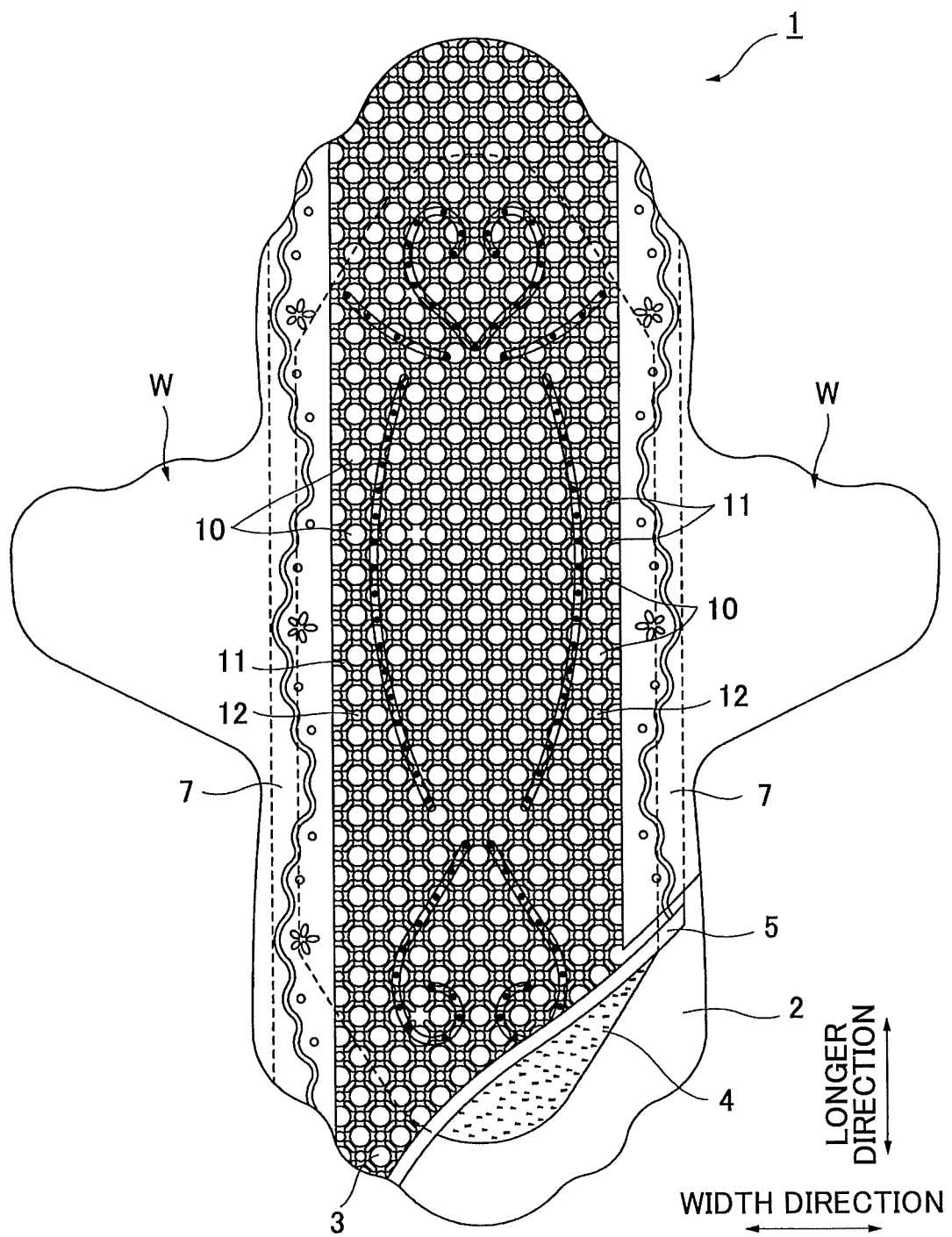
FIG. 7 is a partially broken development view of a sanitary napkin 1 according to a second embodiment.

The second sheet 5 may be arranged with respect to the liquid permeable top sheet 3 in a filled configuration such that the internal spaces of the protruding parts 10 are filled with the second sheet 5 as illustrated in FIG. 4 and FIG. 5. Alternatively, as illustrated in FIG. 6, the second sheet 5 may be arranged in an empty-space configuration such that the flat second sheet 5 may be arranged at the non-skin side of the liquid permeable top sheet 3 having the protruding parts 10 to provide spaces between the liquid permeable top sheet 3 and the second sheet 5. A filled configuration may be formed by applying the embossed parts 11 to the skin side of the bulky second sheet 5 in a state of stacking the liquid permeable top sheet 3 to compress areas other than the protruding parts 10 and to cause the protruding parts 10 to relatively protrude towards the skin side. Alternatively, a filled configuration may be formed by constituting the second sheet 5 with a heat-shrinkable fiber and by applying heat at the pressure time of the embossed parts 11 such that the fiber of the embossed parts 11 thermally shrinks and the protruding parts 10, which do not thermally shrink, are caused to relatively protrude towards the skin side. By filling the spatial portions in the protruding parts 10 with the second sheet 5, cushioning characteristics of the protruding parts 10 are increased and the protruding parts 10 become less likely to be crushed even when pressure is applied to the protruding parts 10. On the other hand, an empty-space configuration may be formed by causing the liquid permeable top sheet 3 to pass between a protruding roll, having multiple protruding parts on its roll surface, and a recessed roll, having multiple recessed parts on its roll surface into which the protruding parts are fitted, and by joining the second sheet 5 to the non-skin side of the liquid permeable top sheet 3 formed in a protruding-recessed shape. By making the hollow spaces inside the protruding parts 10, a feeling in contacting with a skin becomes softened. Further, although it is not illustrated, the liquid permeable top sheet 3 and the second sheet 5 may be caused to protrude together towards the skin side so as to form hollow spaces between the second sheet 5 and the absorbent 4.

The protruding parts 10 are portions formed by protruding at least the liquid permeable top sheet 3 towards the skin side in a protruding shape (dome shape). Although the inner parts of the protruding parts 10 may be empty as described above, it is preferable to form a filled configuration in which the inner parts of the protruding parts 10 are filled with the second sheet 5 in order to enhance cushioning characteristics, as illustrated in FIG. 4 and FIG. 5. Although a planar shape of each of the protruding parts 10 is preferably circular as in the illustrated example, a planar shape of each of the protruding parts 10 may be elliptical or polygonal. Although the protruding parts 10 are arranged in a zigzag pattern, in which the protruding parts 10 are alternately shifted by half pitch for each line in the plan view of FIG. 3, the protruding parts 10 may be arrayed vertically and horizontally to be arranged in a square grid pattern (not illustrated). In a case where the protruding parts 10 are arranged in a square grid pattern, it is preferable that the opening parts 12 are also arranged in a square grid pattern by providing each one of the opening parts 12 at the central part of an area four sides of which are surrounded by the protruding parts 10. By providing the protruding parts 10, a contact area with a skin is reduced and cushioning characteristics are increased. Therefore, a texture feeling becomes favorable.

Along base end parts around the protruding parts 10, the embossed parts 11 and the opening parts 12 are independently arranged at predetermined intervals to surround the protruding parts 10.

The embossed parts 11 are, between the adjacent protruding parts 10, portions recessed towards the non-skin side, relative to the peripheries of the opening parts 12, by compression from the skin side of the liquid permeable top sheet 3. As described above, in a case where the second sheet 5 is disposed at the non-skin side of the liquid permeable top sheet 3, the embossed parts 11 are formed by compressing the liquid permeable top sheet 3 and the second sheet 5 together from the skin side of the liquid permeable top sheet 3 in a state in which the liquid permeable top sheet 3 and the second sheet 5 are stacked in layers. It is preferable that the liquid permeable top sheet 3 and the second sheet 5 are joined through thermal fusion bonding for when applying the embossed parts 11. At the embossed parts 11, due to compression at the time of an embossing process, fiber densities of the liquid permeable top sheet 3 and the second sheet 5 are higher than those of portions of the protruding parts 10. Hence, a fiber density gradient occurs such that a fiber density is relatively low at the protruding parts 10 and a fiber density is relatively high at the embossed parts 11. Further, in the vicinities of the embossed parts 11, in addition to the protruding parts 10 being arranged near respective both sides of the directions that connect the adjacent opening parts 12, and the opening parts 12 are arranged at predetermined intervals at respective both sides in the directions that connect the adjacent opening parts 12.

According to the first embodiment, the embossed parts 11 are non-continuously arranged along the directions that connect the adjacent opening parts 12. Specifically, the plurality of embossed parts 11, each of which is substantially circular in a plan view, are arranged to be separate in the directions that connect the adjacent opening parts 12. Although two embossed parts 11 are arranged between the adjacent opening parts 12 in the illustrated example, three or more embossed parts 11 may be arranged. Further, although the embossed parts 11 each of which is substantially circular in a plan view are given in the illustrated example, the embossed parts 11 may be elliptical or polygonal.

A separation distance a between the embossed parts 11 arranged between the adjacent opening parts 12 may be equal to or different from a separation distance b between the embossed part 11, which is adjacent to the opening part 12, and the opening part 12. Preferably, as illustrated in FIG. 3, it is preferable that the separation distance a between the embossed parts 11 is greater than or equal to the separation distance b between the embossed part 11 and the opening part 12 (a≥b). When a≥b, a body fluid diffused to the embossed parts 11 due to the density gradient of the fibers is easily transferred to the absorbent 4 through the adjacent opening parts 12. The separation distance a may be preferably approximately 1 to 2 fold of the separation distance b (a=b to 2b)

By non-continuously arranging the embossed parts 11 between the adjacent opening parts 12, the liquid permeable top sheet 3 is prevented from being hardened by the embossed parts 11 and a soft texture of the liquid permeable top sheet 3 is retained. Further, because an area per one location of each embossed part 11 becomes small, a body fluid diffused to the embossed parts 11 due to the density gradient of the fibers becomes promptly transferred to the absorbent 4 through the embossed parts 11 and the opening parts 12 without remaining at or near the embossed parts 11 of high fiber density. Further, because the multiple fine embossed parts 11 are arranged around the protruding parts 10, an upright property and a shape stability of the protruding parts 10 of which the base ends are the embossed parts 11 can be favorable, cushioning characteristics of the protruding parts 10 can be enhanced, and a texture feeling can be made more comfortable.

The opening parts 12 are through holes formed, at the central parts of areas four sides of which are surrounded by the protruding parts 10, by penetrating at least the skin side surface and the non-skin side surface of the liquid permeable top sheet 3. In a case where the second sheet 5 is arranged adjacent to the non-skin side of the liquid permeable top sheet 3, the opening parts 12 are formed by penetrating the liquid permeable top sheet 3 and the second sheet 5 together. Although the opening parts 12 may be provided at least a central area in a width direction in which a body fluid discharge part of a wearer contacts, it is preferable to provide the opening parts 12 on the entire liquid permeable top sheet 3 as illustrated in FIG. 1. Although a planar shape of each of the opening parts 12 is preferably circular as in the illustrated example, a planar shape of each of the opening parts 12 may be elliptical or polygonal. An area of each of the opening parts 12 is in a range of from 0.01 mm$^2$ to 8 mm$^2$, and preferably in a range of from 1 mm$^2$ to 5 mm$^2$. The opening parts 12 are be applied by stabbing pins penetrating the sheet. It is preferable that, as illustrated in FIG. 3, the sizes (diameters) of the opening parts 12 are made smaller than those of the opening parts 12 so as not to decrease a texture feeling, and are made greater than groove widths (lengths in the directions perpendicular to the directions that connect the adjacent opening parts 12) of the embossed parts 11 so as to allow a highly viscous body fluid to pass.

A mechanism of body fluid absorption by the sanitary napkin 1 having the above described configuration will be described with reference to FIG. 4. According to the sanitary napkin 1, the embossed parts 11 and the opening parts 12 are formed, around the protruding parts 10, to be separate from each other. Therefore, through capillary action due to a density gradient of fibers, a body fluid absorbed by the protruding parts 10 can be promptly diffused towards the embossed parts 11, the body fluid can be easily transferred to the absorbent 4, at the lower layer, through the embossed parts 11 and the opening parts 12, and a liquid residue on the surface can be reduced. Specifically, in a case where a body fluid of low viscosity such as smooth menstrual blood or urine is absorbed, the body fluid absorbed by the protruding parts 10 is diffused to the embossed parts 11 due to a density gradient of the fibers and is transferred towards the absorbent 4, at the lower layer, through the embossed parts 11. On the other hand, in a case where a highly viscous body fluid such as viscous menstrual blood is absorbed, as illustrated in FIG. 4, the body fluid absorbed diffused from the protruding parts 10 to the embossed parts 11 due to a density gradient of the fibers cannot be absorbed at the embossed parts 11 because of the fiber being made into a film. Therefore, the body fluid diffuses in directions that connect the adjacent opening parts along the embossed parts 11 and transfers to the absorbent 4 through the opening parts 12 formed at both end parts of the directions. In this way, because both menstrual blood of low viscosity and menstrual blood of high viscosity transfer towards the absorbent 4, a liquid residue on the surface can be reduced.

Second Embodiment

As illustrated in FIG. 7 to FIG. 10, a liquid permeable top sheet 3 according to the second embodiment is different from the liquid permeable top sheet 3 according to the first embodiment described above in that skin side extending parts 13 are provided at the peripheries of the opening parts 12 such that at least the liquid permeable top sheet 3 protrudes towards the skin side at height lower than heights of the protruding parts 10 and in that the embossed parts 11 are continuously arranged, between the adjacent opening parts 12, along directions that connect the adjacent opening parts 12. These differences may be both employed at the same time, or either of these differences may be employed.

The skin side extending parts 13, formed at the peripheries of the opening parts 12, are portions obtained by causing a sheet material, which extends from around the opening parts 12 to the opening parts 12, to protrude, at the peripheries of the opening parts 12, towards the skin side, and are fluffy portions formed by an opening process of the opening parts 12. Because the tips of the skin side extending parts 13 are fluffy towards the skin side, a body fluid is easily taken into the opening parts 12 through capillary action due to contacting with the body fluid.

The skin side extending parts 13 may be formed by pressing force of pins at the time of stabbing the pins so as to penetrate the liquid permeable top sheet 3 from the non-skin side to the skin side such that a fiber of the opening portions protrudes towards the skin side. Alternatively, after stabbing pins so as to penetrate the liquid permeable top sheet 3 from the skin side to the non-skin side, when the pins are pulled out, a fiber of the opening portions may be caused to protrude towards the skin side to form skin side extending parts 13 by the fiber being pulled back towards the skin side by a frictional force with the pins in accordance with pulling out the pins.

Figure 9:
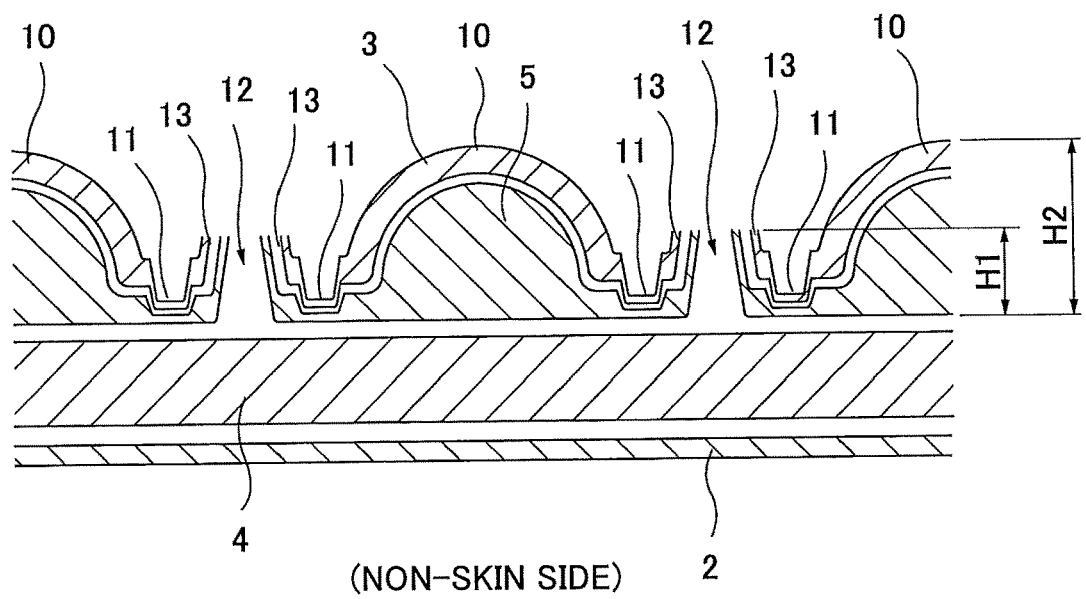
FIG. 9 is a cross-sectional view taken along a line IX-IX of FIG. 8.
Figure 10:
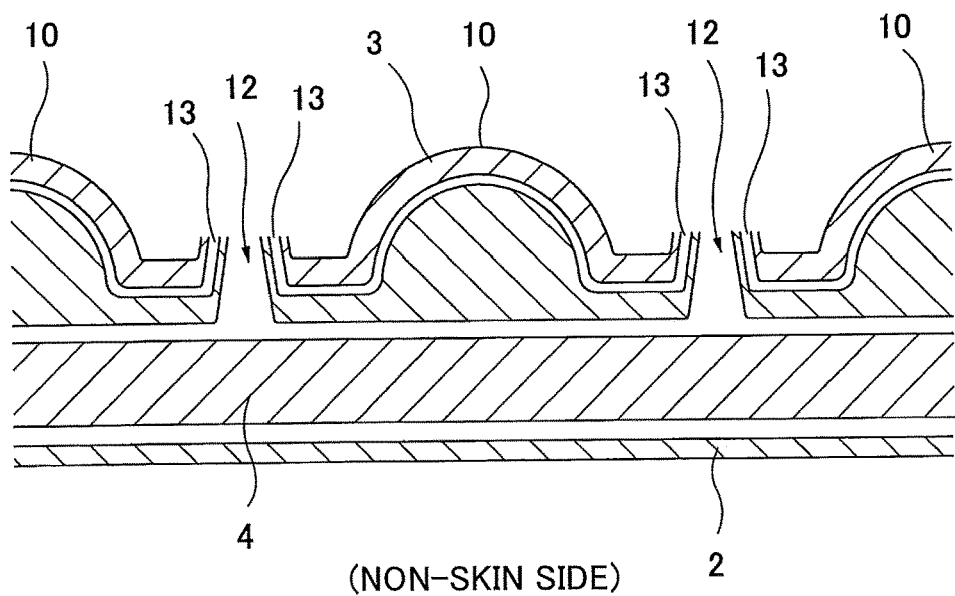
FIG. 10 is a cross-sectional view taken along a line X-X of FIG. 8.

Further, as illustrated in FIG. 9 and FIG. 10, in a case where the second sheet 5 is disposed adjacent to the non-skin side of the liquid permeable top sheet 3, it is preferable that the skin side extending parts 13 are formed by causing the liquid permeable top sheet 3 and the second sheet 5 to protrude together from the peripheries of the opening parts 12 towards the skin side.

The skin side extending parts 13 are formed to be standing substantially vertically from the peripheries of the opening parts 12 or formed such that theirs tips are included inclined towards the centers of the opening parts 12. Accordingly, an area of the tip of each of the skin side extending parts 13 is formed to be substantially equal to or smaller than an area of each of the opening parts 12. Hence, it becomes possible to prevent a body fluid, transferred to the absorbent 4 through the opening part 12, from reversing. On the other hand, at the time of absorbing a body fluid, the body fluid is easily taken into the opening parts 12 by capillary action because the skin side extending parts 13 are provided at the peripheries of the opening parts 12. In a case where the second sheet 5 is arranged at the non-skin side of the liquid permeable top sheet 3, the second sheet 5 is arranged at the inner peripheral side of the skin side extending parts 13 and the liquid permeable top sheet 3 is arranged at the outer peripheral side of the skin side extending parts 13.

The height H1 of the skin side extending parts 13 (height from the non-skin side surface of the second sheet 5 to the tips of the skin side extending parts 13) is formed to be less than the height H2 of the protruding parts 10 (height from the non-skin side surface of the second sheet 5 to the tops of the skin side extending parts 13) (H1<H2). Therefore, when worn by a user, the tips of the skin side extending parts 13 are not in contact with a skin surface and the protruding parts 10 are certainly in contact with the skin surface. Therefore, a favorable texture feeling can be retained. The height H1 of the skin side extending parts 13 is in a range of from 0.05 mm to 2.0 mm and is preferably in a range of from 0.1 mm to 1.5 mm. When the height H1 of the skin side extending part 13 is measured, a layered structure of the liquid permeable top sheet 3 and the second sheet 5 cut to be a predetermined size is set on a stage of a microscope such that the second sheet 5 is located below. Then, the layered structure of the sheets is laterally captured by the microscope to measure a distance between a lower end of the second sheet 5 immediately below the skin side extending part 13 and an upper end of the skin side extending part 13 as the height H1.

By providing the skin side extending parts 13 at the peripheries of the opening parts 12, a body fluid, diffused from the protruding parts 10 to the embossed parts 11 due to a density gradient of the fibers such as a highly viscous body fluid such as viscous menstrual blood in particular, contacts the skin side extending parts 13, contacts the skin side extending parts 13, which protrude towards the skin side at the peripheries of the opening parts 12, is taken into the opening parts 12 through capillary action, and is transferred towards the absorbent 4, at the lower layer.

Figure 8:
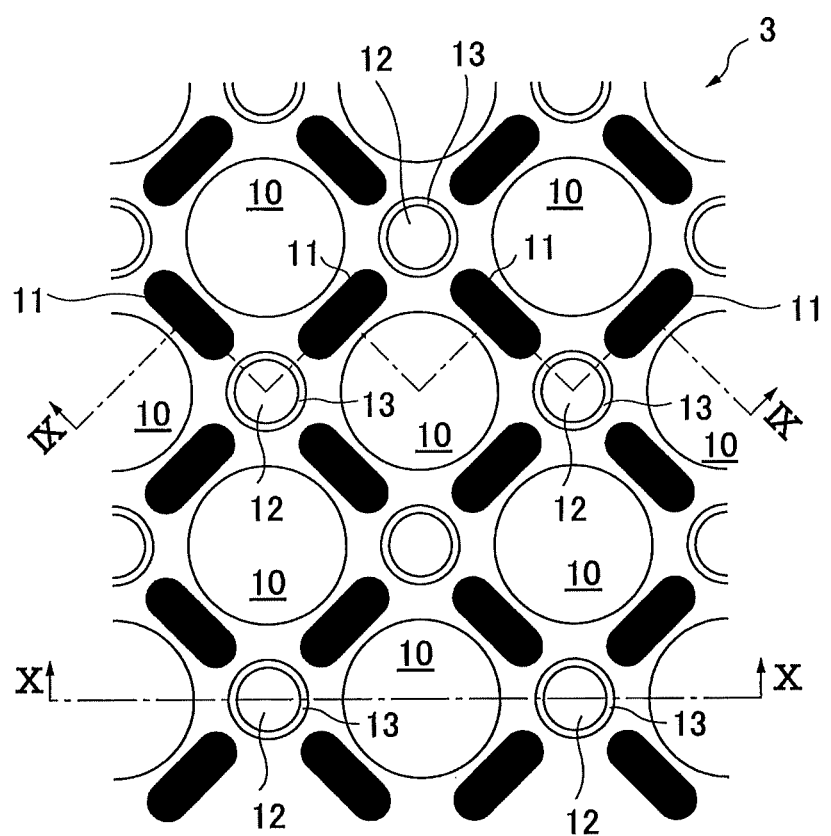
FIG. 8 is an enlarged plan view of a liquid permeable top sheet 3 according to the second embodiment.

Next, the embossed parts 11 will be described. According to the second embodiment, as illustrated in FIG. 8, the embossed parts 11 are continuously formed along the directions that connect the opening parts 12. That is, each one of the embossed parts 11 is arranged between the adjacent opening parts 12, and a planar shape of each of the embossed parts 11 is formed to be a groove shape that is long in a direction that connects the opening parts 12 as illustrated in FIG. 8. Thereby, the protruding parts 10 are arranged adjacent to respective both sides in the lengthwise direction of the groove of each of the embossed parts 11, and the opening parts 12 are arranged, at a predetermined interval, from respective both ends in the lengthwise direction of the groove of each of the embossed parts 11. That is, in a plan view illustrated in FIG. 8, four embossed parts 11 and four opening parts 12 are alternately arranged at substantially equal intervals to surround each protruding part 10.

The embossed parts 11 are formed continuously along the directions that connect the adjacent opening parts 12 such that a body fluid, diffused from the protruding parts 10 to the embossed parts 11 due to the density gradient of the fibers, easily diffuses along the embossed parts 11 in the lengthwise directions of the grooves, and is easily absorbed by the absorbent by passing through the opening parts 12 adjacent to both end parts of the lengthwise directions of the embossed parts 11. Further, in a case where the skin side extending parts 13, which protrude towards the skin side, are formed at the peripheries of the opening parts 12, a body fluid, diffused along the embossed parts 11 in the lengthwise directions of the grooves, contacts the skin side extending parts 13, is taken into the opening parts 12 through capillary action, and is transferred to the absorbent 4, at the lower layer.

Third Embodiment

Figure 11:
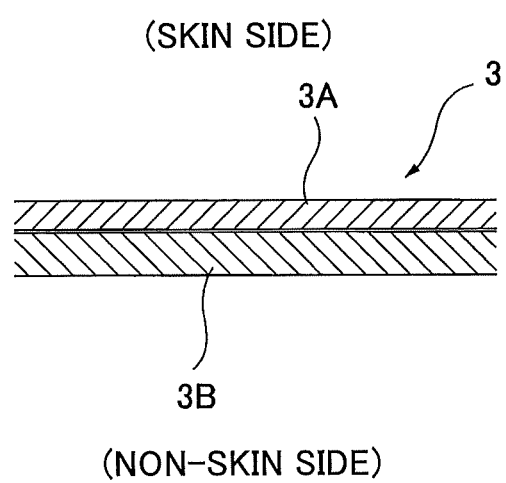
FIG. 11 is a cross-sectional view of a liquid permeable top sheet 3 according to a third embodiment.

A liquid permeable top sheet 3 according to a third embodiment has a layered structure of multiple layers. The liquid permeable top sheet 3 may have a single layer structure. Alternatively, according to the third embodiment, as illustrated in FIG. 11, the liquid permeable top sheet 3 may have a layered structure including a skin side layer 3A located at the skin side and a non-skin side layer 3B located at the non-skin side. Although the illustrated example has a two-layer structure of the skin side layer 3A and the non-skin side layer 3B, one or more intermediate layers may be provided between the skin side layer 3A and the non-skin side layer 3B to form a multiple layers structure of three or more layers. Then, it is preferable that a fineness of a fiber constituting the skin side layer 3A is a fine fiber of less than 2.0 dtex. Thereby, friction with a skin can be reduced and a texture feeling can be further favorable.

Further, it is preferable that the fineness of a fiber constituting the non-skin side layer 3B is greater than the fineness of a fiber constituting the skin side layer 3A. It is more preferable that the fineness of a fiber constituting the non-skin side layer 3B is greater than the fineness of a fiber constituting the second sheet 5. Specifically, it is preferable that a fineness of a fiber constituting the non-skin side layer 3B is approximately 3.3 dtex, and a fineness of a fiber constituting the second sheet 5 is approximately 2.2 dtex, which is less than the fineness of the fiber constituting the non-skin side layer 3B. Thereby, a body fluid can be easily transferred due to a density gradient of fibers from the non-skin side layer 3B of the liquid permeable top sheet 3 to the second sheet 5, and a liquid residue on the surface can be further reduced, and in a case where the skin side extending parts 13 are formed at the peripheries of the opening parts 12, a body fluid easily permeates in the openings.

A basis weight of the skin side layer 3A of the liquid permeable top sheet 3 is in a range of from 5 $g/m^2$ to 20 $g/m^2$, and is preferably approximately 8 $g/m^2$. A basis weight of the non-skin side layer 3B is in a range of from 10 $g/m^2$ to 25 $g/m^2$, and is preferably approximately 17 $g/m^2$. A basis weight of the second sheet 5 is in a range of from 15 $g/m^2$ to 60 $g/m^2$, and is preferably in a range of from approximately 18 $g/m^2$ to 30 $g/m^2$.

In a case where the liquid permeable top sheet 3 has a two-layer structure of the skin side layer 3A and the non-skin side layer 3B, and the second sheet 5 is disposed adjacent to the non-skin side of the non-skin side layer 3B, it is preferable to set strength of durability of hydrophilic oil of the skin side layer 3A, the non-skin side layer 3B, and the second sheet 5 to be in a relationship of the skin side layer 3A the non-skin side layer 3B the second sheet 5. Thereby, the strength of durability of hydrophilic oil is enhanced towards lower layers (towards the second sheet 5), a body fluid can easily permeate the second sheet 5 from the skin side layer 3A of the liquid permeable top sheet 3, and a liquid residue on the surface can be reduced. The strength of durability of hydrophilic oil means a degree by which hydrophilic oil maintains a state of being fixed to a fiber without dropping and outflowing together with a liquid from the fiber surface at the time of liquid passage. When the strength is low, it means that hydrophilic oil easily outflows together with a liquid at the time of passage of the liquid.

For example, an anionic surfactant, a carboxylate, an acylated hydrolyzed protein, a sulfonate, a sulfate ester salt, a phosphate ester salt, a nonionic surfactant, a polyoxyethylene surfactant, a carboxylate ester, a carboxylic acid amide, a polyalkylene oxide block copolymer, a cationic surfactant, a quaternized ammonium salt, an amphoteric surfactant, an imidazolinium derivative, or the like may be the above described hydrophilic oil. In addition, a known agent applied as hydrophilic oil to a fiber may be widely applied.

Examples of the application method of the hydrophilic oil may include an application by a spray, coating by gravure printing or flexo printing, and curtain coating by various coaters. The hydrophilic oil may be mixed at a step of fibers. Note that in order to cause a body fluid to easily permeate the absorbent 4, it is preferable to set hydrophilic properties to have a relationship of the skin side layer 3A the non-skin side layer 3B the second sheet 5. The hydrophilic properties may be adjusted by adjusting the amount of hydrophilic oil that is applied. The strength of durability of hydrophilic oil may be adjusted by using, in combination with hydrophilic oil, an acrylic water-soluble resin, a rubber-based latex, a urethane-based resin, a polyester-based resin, a polyvinyl-based resin or the like as an adhesive resin or as a catalyst and by adjusting these additive amounts.

The above described strength of durability of hydrophilic oil can be evaluated by a ten-point method. According to this ten-point method, a sample is placed on eight pieces of stacked filter paper such that the side, to be in contact with a skin, of the sample is upward, and a ten-point measurement plate, which has ten circular voids of which diameters are 15 mm and thicknesses are 5 mm, is placed on the sample. Then, each of the voids of the ten-point measurement plate is filled with artificial menstrual blood of 37° C., the number of voids in which the artificial menstrual blood remains without being absorbed within two seconds is counted, and this count is repeated for every three minutes to count the number N of times (number of repetitions) until which the artificial menstrual blood remains in all the ten voids, for evaluation. As the number N of times decreases, the strength of durability of hydrophilic oil decreases. Note that the above described artificial menstrual blood has a composition made of 12.30% by weight of glycerin, 85.18% by weight of de-ionized water, 0.45% by weight of CMC (carboxymethyl cellulose sodium), 0.97% by weight of NaCl (sodium chloride), 1.04% by weight of $Na_2CO^3$(Sodium carbonate), and 0.06% by weight of water bloom.

Fourth Embodiment

Figure 12:
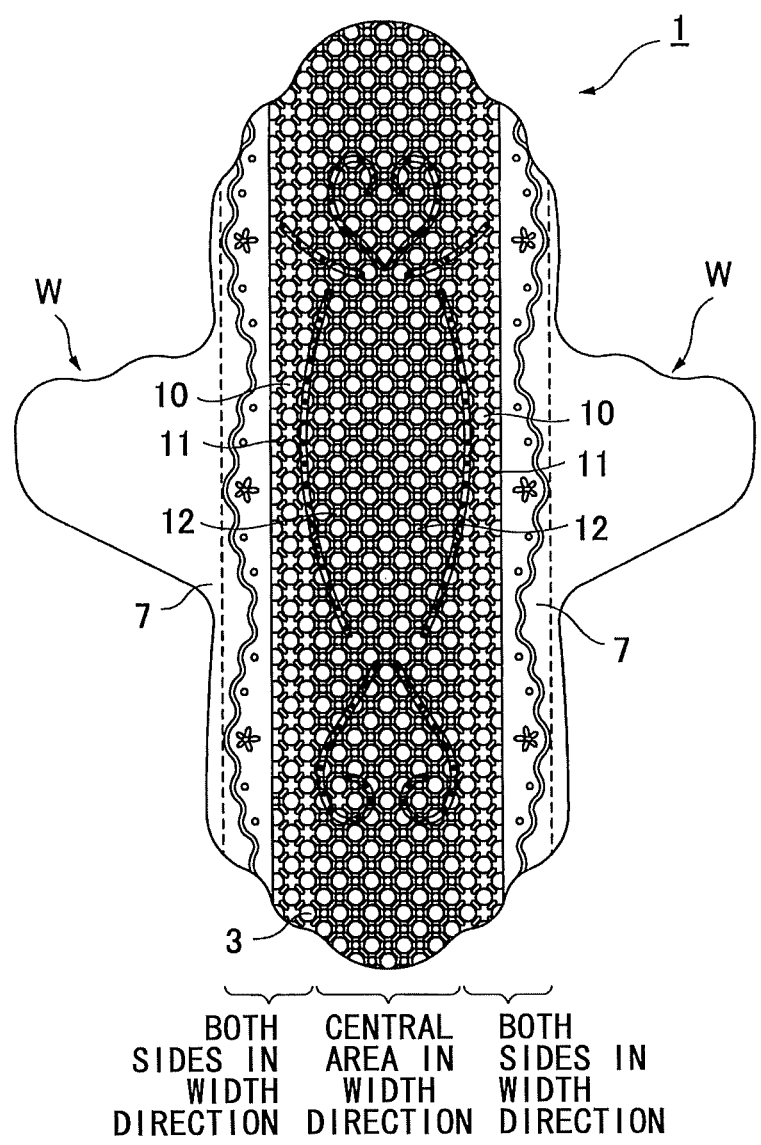
FIG. 12 is a development view of a sanitary napkin 1 according to a fourth embodiment.

According to a liquid permeable top sheet 3 of a fourth embodiment, a region in which the opening parts 12 are provided is only a central area in the width direction, or sizes of the opening parts 12 at a central area in the width direction are larger than those at other areas. The region in which the opening parts 12 are provided may be an entire region of the liquid permeable top sheet 3 as illustrated in FIG. 1, or may be, as illustrated in FIG. 12 of the fourth embodiment, only a central area in the width direction that includes a region for contacting a body fluid discharge part of a wearer without providing a region for the opening parts 12 at outer areas relative to the central area in the width direction. Further, the opening diameters of the opening parts 12 may be substantially equal over the entire surface. Alternatively, as in a variation example of the fourth embodiment, opening diameters at a central area in the width direction may be larger than opening diameters at both side areas in the width direction. Because discharged menstrual blood is mainly absorbed in a central area in the width direction, the body fluid can be promptly absorbed by enlarging the sizes of the opening parts 12 at the central area in the width direction.

DESCRIPTION OF REFERENCE SYMBOLS 1 sanitary napkin
2 liquid impermeable back sheet
3 liquid permeable top sheet
4 absorbent
5 second sheet
10 protruding part
11 embossed part
12 opening part
13 skin side extending part

The invention claimed is:

1. An absorbent article comprising:
an absorbent interposed between a liquid permeable top sheet and a back sheet,
wherein the liquid permeable top sheet has multiple protruding parts that protrude towards a skin side and that are formed at intervals, embossed parts compressed from the skin side, and opening parts that penetrate the liquid permeable top sheet, the embossed parts and the opening parts being formed, around the protruding parts, to be separate from each other,
wherein, in plan view, each of the opening parts is arranged at an area of which four sides are surrounded by corresponding four of the protruding parts, and one or more of the embossed parts are arranged between the opening parts adjacent to each other along directions that connect the opening parts, and
wherein the four sides of the area, at which each of the opening parts is arranged, are immediately adjacent to the corresponding four of the protruding parts.

2. The absorbent article according to claim 1, wherein skin side extending parts are provided at peripheries of the opening pans such that the liquid permeable top sheet protrudes towards the skin side at heights lower than heights of the protruding parts.

3. The absorbent article according to claim 1, wherein in a plan view of the liquid permeable top sheet, the protruding parts are arranged in a zigzag pattern and the embossed parts are continuously or non-continuously arranged, between the adjacent opening parts, along the directions that connect the adjacent opening parts.

4. The absorbent article according to claim 1, wherein the liquid permeable top sheet has a layered structure including a skin side layer located at the skin side and a non-skin side layer located at a non-skin side, a fineness of a fiber constituting the non-skin side layer is less than 2.0 dtex.

5. The absorbent article according to claim 1, wherein
a second sheet is disposed adjacent to a non-skin side of the liquid permeable top sheet, and
the embossed parts are formed by compressing the liquid permeable top sheet and the second sheet together, and the opening parts are formed by penetrating the liquid permeable top sheet and the second sheet together.

6. The absorbent article according to claim 5, wherein skin side extending parts that protrude towards the skin side are provided at peripheries of the opening parts, heights of the skin side extending parts being lower than heights of the protruding parts, the skin side extending; parts being formed such that the liquid permeable top sheet and the second sheet protrude towards the skin side from the peripheries of the opening parts.

7. The absorbent article according to claim 1, wherein
the liquid permeable top sheet has a layered structure including a skin side layer located at the skin side and a non-skin side layer located at a non-skin side, and a second sheet is disposed adjacent to a non-skin side of the non-skin side layer, and
a fineness of a fiber constituting the non-skin side layer is set to be greater than a fineness of a fiber constituting the second sheet.

8. The absorbent article according to claim 1, wherein
the liquid permeable top sheet has a layered structure including a skin side layer located at the skin side and a non-skin side layer located at a non-skin side, and a second sheet is disposed adjacent to a non-skin side of the non-skin side layer, and
strength of durability of hydrophilic oil of the skin side layer of the liquid permeable top sheet, the non-skin side layer of the liquid permeable top sheet, and the second sheet is in a relationship of the skin side layer the non-skin side layer≤the second sheet.

9. The absorbent article according to claim 1, wherein the one or more of the plurality of embossed parts or one of the protruding parts is arranged between each adjacent two of the opening parts.

\* \* \* \* \*